United States Patent [19]

Rosencwaig et al.

[11] Patent Number: 5,596,406
[45] Date of Patent: Jan. 21, 1997

[54] SAMPLE CHARACTERISTIC ANALYSIS UTILIZING MULTI WAVELENGTH AND MULTI ANGLE POLARIZATION AND MAGNITUDE CHANGE DETECTION

[75] Inventors: Allan Rosencwaig, Danville; David L. Willenborg, Dublin, both of Calif.

[73] Assignee: Therma-Wave, Inc., Fremont, Calif.

[21] Appl. No.: 532,871

[22] Filed: Aug. 15, 1995

Related U.S. Application Data

[60] Continuation of Ser. No. 368,420, Jan. 4, 1995, abandoned, which is a division of Ser. No. 93,178, Jul. 16, 1993, Pat. No. 5,412,473.

[51] Int. Cl.⁶ ............................. G01J 4/00; G01J 3/28
[52] U.S. Cl. ................... 356/327; 356/328; 356/367
[58] Field of Search ............................... 356/364, 369, 356/367, 326–328

[56] References Cited

U.S. PATENT DOCUMENTS

| | | | |
|---|---|---|---|
| 3,527,536 | 9/1970 | Alpen | 356/72 |
| 3,904,293 | 9/1975 | Gee | 356/118 |
| 4,210,401 | 7/1980 | Batteu | 356/369 |
| 4,653,924 | 3/1987 | Itonaga et al. | 356/369 |
| 4,872,758 | 10/1989 | Miyazaki et al. | 356/381 |
| 4,999,014 | 3/1991 | Gold et al. | 356/382 |
| 5,003,500 | 3/1991 | Gerber | 356/326 |
| 5,018,863 | 5/1991 | Vareille et al. | 356/369 |
| 5,042,951 | 8/1991 | Gold et al. | 356/369 |
| 5,159,412 | 10/1992 | Willenborg et al. | 356/445 |
| 5,166,752 | 11/1992 | Spanier et al. | 356/369 |
| 5,181,080 | 1/1993 | Fanton et al. | 356/381 |
| 5,185,638 | 2/1993 | Conzola et al. | 356/340 |
| 5,291,269 | 3/1994 | Ledger | 356/355 |
| 5,373,359 | 12/1994 | Woollam et al. | 356/369 |
| 5,406,371 | 4/1995 | Sakai et al. | 356/364 |
| 5,416,594 | 5/1995 | Gross et al. | 356/237 |
| 5,526,117 | 6/1996 | Wielsch et al. | 356/369 |

FOREIGN PATENT DOCUMENTS

| | | |
|---|---|---|
| 265226 | 9/1987 | Germany. |
| 9300956.9 | 5/1993 | Germany. |
| 4301889 | 7/1994 | Germany. |
| 61-182507 | 8/1986 | Japan. |
| 63-140940 | 6/1988 | Japan ............................ G01N 21/21 |
| 64-23126 | 1/1989 | Japan ............................ G01J 4/00 |
| 64-33602 | 3/1989 | Japan ............................ G01B 11/06 |
| 2-24502 | 1/1990 | Japan ............................ G01B 11/06 |
| 4-294226 | 10/1992 | Japan ............................ G01J 4/04 |
| 5-71923 | 3/1993 | Japan ............................ G01B 11/06 |
| 2088552 | 6/1982 | United Kingdom ................... 356/369 |
| 92012404 | 7/1992 | WIPO ................................... 356/369 |

OTHER PUBLICATIONS

H. H. Bloem, W. E. Goetz, R. N. Jackson & R. W. Kern, "Development of an Automatic Ellipsometer," *Electro-Optical Systems Design*, Mar. 1980, vol. 2450, pp. 38–45.

J. Horkans, B. D. Cahan & E. Yeager, "Electrode potential scanning ellipsometric spectroscopy: study of the formation of the anodic oxide film on noble metals," *Surface Science*, 1974, vol. 46, pp. 1–23.

(List continued on next page.)

*Primary Examiner*—Georgia Y. Epps
*Assistant Examiner*—Jason D. Eisenberg
*Attorney, Agent, or Firm*—Limbach & Limbach L.L.P.

[57] ABSTRACT

An optical measurement device is disclosed for evaluating the parameters of a sample. The device includes a polychromatic source for generating a probe beam. The probe beam is focused on the sample surface. Individual rays within the reflected probe beam are simultaneously analyzed as a function of the position within the beam to provide information at multiple wavelengths. A filter, dispersion element and a two-dimensional photodetector array may be used so that the beam may be simultaneously analyzed at multiple angles of incidence and at multiple wavelengths. A variable image filter is also disclosed which allows a selection to be made as to the size of the area of the sample to be evaluated.

9 Claims, 4 Drawing Sheets

OTHER PUBLICATIONS

I. An, H. V. Nguyen, A. R. Heyd & R. W. Collins, "Simultaneous real time spectroscopic ellipsometry and reflectance for monitoring semiconductor and thin film preparation, " *Mat. Res. Soc. Symp. Proc.*, 1994 Materials Research Society, vol. 324, pp. 33–38.

D. K. Burge & H. E. Bennett, "Effect of a Thin Surface Film on the Ellipsometric Determination of Optical Constants, " *Journal of the Optical Society of America*, Dec. 1964, vol. 54, pp. 1428–1433.

W.-K. Paik & J. O'M. Bockris, "Exact ellipsometric measurement of thickness and optical properties of a thin light–absorbing film without auxiliary measurements, " *Surface Science*, 1971, vol. 28, pp. 61–68.

B. D. Cahan, "Implications of three parameter solutions to the three–layer model, " *Surface Science*, 1976, vol. 56, pp. 354–372.

A. Hamnett & S. J. Higgins, "An ellipsometric study of polypyrrole films on platinum, " *J. Electroanal. Chem.*, 1989, vol. 270, pp. 479–488.

R. P. Netterfield, P. J. Martin, W. G. Sainty, R. M. Duffy & C. G. Pacey, "Characterization of growing thin films by in situ ellipsometry, spectral reflectance and transmittance measurements, and ion–scattering spectroscopy, " *Rev. Sci. Instrum.*, Nov. 1985, vol. 56, No. 11, pp. 1995–2003.

F. Hazebroek & W. M. Visser, "Automated laser interferometric ellipsometry and precisionreflectometry, " *J. Phys. E. Sci. Instrum*, vol. 16, 1983, pp. 654–661.

P. S. Hauge, "Optical Film Thickness Measurement Tool, " *IBM Technical Disclosure Bulletin*, vol. 21, No. 2, Jul. 1978, pp. 884–885.

"Apparatus and Method for Film Thickness and Optical Constant Determination, " *IBM Technical Disclosure Bulletin*, vol. 31, No. 8, Jan. 1989, pp. 363–368.

Dr. R. F. Spanier, "Elliposmetry A Century Old New Technique, " *Industrial Research*, Sep. 1975, pp. 73–76.

Spindler & Hoyer Brochure, "Retardation Plates, " pp. S15–S20.

A. F. H. Goetz, "High Resolution Imaging Spectrometer (HIRIS): Science and Instrument, " *International Journal of Imaging Systems and Technology*, vol. 3, 1991, pp. 131–143.

M. Herring, J. E. Duval & S. A. Macenka, "Development of the imaging spectrometer: technical challenges and solutions, " *Optical Systems for Space Applications*, SPIE vol. 810, pp. 100–111.

Patent Cooperation Treaty PCT International Search Report, date of mailing Nov. 11, 1994, 7 pages in length.

SAMPLE CHARACTERISTIC ANALYSIS UTILIZING MULTI WAVELENGTH AND MULTI ANGLE POLARIZATION AND MAGNITUDE CHANGE DETECTION

This is a continuation of application Ser. No. 08/368,420 filed on Jan. 4, 1995, now abandoned, which in turn is a divisional of Ser. No. 08/093,178, filed Jul. 16, 1993 now U.S. Pat. No. 5,412,473, issued May 2, 1993.

TECHNICAL FIELD

The subject invention relates to an analyzer particularly suited for evaluating parameters of a thin film sample. The apparatus is capable of performing simultaneous, multiple angle of incidence measurements at multiple wavelengths.

BACKGROUND OF THE INVENTION

In the prior art, there has been considerable interest in developing methods and apparatus for evaluating the composition and thickness of thin films on a substrate. This need is particularly acute in the semiconductor manufacturing industry where extremely thin films are deposited on a silicon substrate.

The preferred devices rely on non-contact, optical measurement techniques. In these devices, a probe beam is directed to the sample, and a particular parameter of the reflected probe beam is measured. For example, it is known that as the thickness of the film varies, the intensity of the reflected probe beam will vary due to the variation in interference effects created at the interface between the thin film and the substrate. It is also known that the thickness of the thin film will have an effect on the change in polarization state which occurs when the probe beam is reflected off the sample surface. Thus, by monitoring either the change in intensity of the reflected probe beam or its change in polarization state (ellipsometry), information about the thin film can be derived.

In most devices, some form of multiple measurements are desirable in order to increase accuracy. One such approach for gaining additional accuracy is to obtain measurements at a number of different wavelengths. A spectrophotometer is designed to provide interferometric type measurements at various wavelengths. Another approach for gaining additional accuracy is to take measurements at a number of different angles of incidence of the probe beam.

Until quite recently, the mechanisms for generating measurements at multiple angles of incidence were quite cumbersome. More specifically, the equipment had to be designed so that the angle between the probe beam optics and the sample could be varied.

It has been found that these difficulties can be overcome by extracting angular information from rays within the reflected probe beam. This approach is described in detail in U.S. Pat. Nos. 4,999,014 and 5,042,951, assigned to the same assignee herein and incorporated by reference. As described in these patents, the light from the probe beam is tightly focused on the sample surface in a manner to create a spread of angles of incidence for individual rays within the focused probe beam. After reflection, individual rays within the probe beam are analyzed, with the radial position of the rays within the probe beam being related to the angle of incidence of the beam on the sample surface. Preferably, a photodetector having an array of individual elements is used to measure rays having different angles of incidence. This approach can be used in both interferometric and ellipsometric analyses.

In the preferred embodiments discussed in the above identified patents, the probe beam was generated by a laser having an output that was substantially diffraction limited allowing focusing to a spot size on the order of one micron in diameter. This approach provides high spatial resolution permitting analysis of extremely small regions on the sample.

In many cases, such high spatial resolution is unnecessary. In fact, in some analyses, the semiconductor manufacturer is only interested in measurements of average conditions over a much larger region. In the latter case, it would be possible to use a non-diffraction limited light source such as an arc lamp or other white light source.

One advantage which is obtained when utilizing a white light source is that additional measurements can be taken at different wavelengths, in a manner analogous to commercially available spectrophotometers. In these devices, a means is provided for sequentially or simultaneously selecting a plurality of individual wavelengths. The means can include various combinations of filters, gratings or prisms.

As can be appreciated, the need to provide wavelength selective elements adds to the cost and complexity of the apparatus as well as requiring moving parts. More significantly, the need to take sequential measurements slows the operation of the device. Therefore, it would be desirable to be able to obtain simultaneous measurements not only at different angles, but at different wavelengths as well.

One approach that was suggested for achieving this goal is set forth in U.S. Pat. No. 5,166,752, to Spanier, which is incorporated herein by reference. The device disclosed therein is a simultaneous multiple angle of incidence ellipsometer. One embodiment of the device includes a polychromatic light source. FIG. 5 of the patent illustrates a method by which it is suggested that simultaneous measurements can be made at both multiple angles of incidence and at multiple wavelengths. This approach includes providing a dispersing element for spreading out the beam as a function of wavelength. The beam is then directed to a photodetector having a two dimensional array of individual detector elements. The array is oriented so that each column measures light from only a narrow band of wavelengths at a plurality of angles of incidence. In contrast, each row is arranged to obtain measurements at a single angle of incidence at various wavelengths.

The approach described in the Spanier patent was suggested because of the desire to generate simultaneous measurements at various angles of incidence and at various wavelengths without scanning either variable. However, the results that can be achieved using the approach described in Spanier are less than ideal. The problems associated with the Spanier proposal can best be understood by referring to FIG. 1 herein. FIG. 1 illustrates a two dimensional photodetector array 10 of the type proposed by Spanier. The array includes a plurality of rows 6 and columns 8 of detector elements. Superimposed on top of the array are the foot prints of two different probe beams (2 and 4) having different wavelengths. The pattern of the probe beams (2, 4) would be of the type created using a dispersing element to spatially separate the wavelengths in a polychromatic beam. In this illustration, the dispersing element is oriented in a manner to separate light of different wavelengths along a vertical axis so that the detector elements across each row 6 measure light as a function of angle of incidence.

Arrow A in FIG. 1 is aligned with the row of photodetector elements associated with the central diameter of beam 2. As taught in the above cited patents of the assignee, the angle of incidence measured by any individual detector element in the row is based on the its radial position with respect to the beam. Specifically, the radial position (R) is proportional to sinθ/M where θ is the angle of incidence and M is equal to the maximum angle and is given by the following equation:

$$R = R_M (\sin\theta / \sin\theta_M) \tag{1}$$

Based on these relationships, it can be seen that the center detector element 12 will correspond to the central angle of incidence of the beam. The left and right-hand detector elements 14 and 16 will correspond to the maximum and minimum angles of incidence in the beam. In the assignees preferred design, wherein the beam is focused normal to the surface of the sample with a high numerical aperture lens (i.e., 0.90 NA), the spread of angles of incidence is on the order of 128 degrees. In this case, the detector elements 14 and 16 at the radially outermost points on the beam will measure rays having angles of incidence of +64 degrees and −64 degrees.

The problems of the Spanier design can best be appreciated by considering the light falling on an intermediate element 18 where the two beams overlap. For beam 2, element 18 lies halfway between the center and the edge of the radius of the beam. In a system having a probe beam at normal incidence and a half angle spread of 64 degrees, the angle of incidence of a ray falling halfway between the center and the edge of a beam would be on the order of 27 degrees.

As can be seen in FIG. 1, the light falling on element 18 is not limited to light associated with the wavelength of beam 2. Rather, light from beam 4 of an adjacent wavelength falls on element 18 as well. Having light of different wavelengths fall on individual detector elements will complicate the wavelength dependent analysis of the sample. More significantly, the light falling on element 18 from beam 4 corresponds to a substantially different angle of incidence than the light from beam 2. This difference can be appreciated by comparing the radial distance between the center of beam 2 and element 18 (R1) with the radial distance between the center of beam 4 and element 18 (R2). As can be seen, the radial distance R2 is significantly greater than the radial distance R1. Recalling that the angle of incidence is directly related to the radial position of the rays within the beam, it can be seen that the angle of incidence for the light ray of the wavelength of beam 4 at element 18 is larger than the angle of incidence for the ray associated with beam 2 at element 18. In the illustrated example, the angle of incidence of the ray for beam 4 at element 18 would be on the order of 46 degrees as compared to the 27 degrees for beam 2.

The example illustrated in FIG. 1 is simplified in that only two wavelength beams are shown. In reality, there will be multiple overlapping beams. Thus, the approach described in Spanier results in each detector element detecting light not only from multiple wavelengths but many different angles of incidence as well. This overlap results in a substantial blurring of the data preventing an adequate analysis of the sample. Accordingly, it would be desirable to provide a detection approach which provides significant isolation for the wavelength and angle of incidence measurements.

Therefore, it is one object of the subject invention to provide an improved method for simultaneously measuring both angle and wavelength information contained in a reflected probe beam.

It is a further object of the subject invention to provide a method of simultaneously measuring angle and wavelength information which can be used in both interferometric and ellipsometric devices.

It is still a further object of the subject invention to provide a simultaneous multiple angle of incidence interferometric device which generates measurements at a plurality of selected wavelengths.

Another aspect of the subject invention relates to an approach for easily varying the area on the sample over which measurements are taken. As noted above, when using a laser to generate the probe beam, a spot size on the order of one micron can be obtained using a fast lens. When using a white light source, such tight focusing is not possible and a much wider area is illuminated. When using a high numerical aperture lens in a configuration as described in the assignees two prior patents, the minimum focused spot size which could be achieved with a white light source would be on the order of 150 microns in diameter.

Accordingly, it would be desireable to provide a system wherein the selected measurement region can be less than the minimum focused spot size diameter. Moreover, it would be desirable to provide a device wherein the size of the measurement region can be easily changed without moving or replacing the lens elements.

SUMMARY OF THE INVENTION

In accordance with these and other objects, the subject invention relates to a simultaneous multiple angle of incidence measurement device, particularly suited for evaluating thin films on semiconductors. As will be seen below, the advances discussed herein can be used on both interferometric and ellipsometric devices.

Both aspects of the subject invention relate to the use of white light sources with simultaneous multiple angle of incidence measurement devices. The use of a white light source allows measurements to be taken at multiple wavelengths.

One problem associated with a non-coherent white light source is that the focused spot size tends to be larger than that which can be achieved using a coherent laser source. In accordance with the subject invention, the area of measurement can be reduced using a variable image filter located in the path of the reflected beam and prior to the detector. The variable image filter consists of a combination of a relay lens and an aperture plate. The aperture plate is located in the focal plane of the lens. The relay lens projects an image of the beam as it exists on the sample surface onto the aperture plate. By selecting the focal power of the relay lens and the size of the aperture, the desired size of the imaged region can be controlled.

It should be noted that the concept of using a variable image filter in these type of devices was disclosed in U.S. Pat. No. 5,159,412, assigned to the assignee herein and incorporated by reference. In that disclosure, the variable image filter was utilized to limit spurious reflections returning from outside the focused laser beam spot from reaching the detector. The subject invention differs from the prior disclosure in that the variable image filter herein is used to image a region smaller than the focused white light spot. More significantly, in the preferred embodiment disclosed herein, the variable image filter is provided with a plurality of aperture plates allowing the size of the imaged region to be easily selected by the operator without having to change and/or reposition the lens elements.

In another aspect of the subject invention, a method is disclosed for improving simultaneous multiple wavelength measurements in devices which also simultaneously measure light at multiple angles of incidence. The system is applicable to either interferometric or ellipsometric devices.

The measurement device will include a polychromatic light source for generating a probe beam of radiation. A microscope objective is used to focus the probe beam on the sample in a manner to create a spread of angles of incidence. A detector is provided to analyze the reflected probe beam. In an interferometric device, the detector will measure the intensity of the beam. In an ellipsometer, the detector components will determine the change in polarization state which occurs when the beam interacts with the sample. In the principal embodiment, the detector will measure various rays as a function of their radial position within the reflected probe beam to provide specific data on different angles of incidence with respect to the sample surface.

As in the prior art approach, a wavelength dispersion element is located in the path of the reflected probe beam. The dispersion element functions to angularly spread the beam as a function of wavelength. In the principal embodiment, the detector includes a two dimensional array of elements, wherein each row of elements measures the full angle of incidence information for a different central wavelength.

In order to reduce the problem of overlapping angle of incidence measurements, a filter is located in the path of the reflected probe beam, prior to the dispersion element. The filter includes a narrow rectangular aperture aligned along a diameter of the beam. The aperture should be oriented to be perpendicular to the plane in which the dispersion element angularly spreads the light. The dimensions of the aperture are selected to transmit a narrow cross-section of the beam that when imaged on the detector will correspond to the width of one row of detector elements. Preferably, the aperture should transmit only about ten percent of the total cross-section of the beam.

In order to preserve the angle of incidence information in the transmitted cross-section of the beam, it is also necessary to position the filter in a relay image plane of the exit pupil of the microscope objective focusing lens. In this relay image plane, all of the angles of incidence have a one to one correspondence with the positions of the rays on the beam spot on the sample surface.

The narrow aperture substantially reduces the amount of overlap between beams of different wavelengths. Any overlap which occurs is limited to wavelengths which are close, minimizing the adverse affect on wavelength dependent calculations. Moreover, the adverse impact of overlapping wavelength information is almost fully eliminated because there is no overlap of different angle of incidence information. More specifically, since the slit filter is arranged so that the only light passing through is along a single beam diameter, the radial distance from the center of the transmitted rectangular cross-section to a given detector element illuminated by that beam will be essentially the same for any wavelength. If the radial distance is the same for all wavelengths, then the angle of incidence of the light rays striking that detector element are the same as well. Therefore, the detector assembly provides isolation for simultaneous multiple angles of incidence measurements while simultaneously measuring multiple wavelengths.

In the preferred embodiment, the probe beam light is linearly polarized and a spherical objective is used to focus the light on the sample surface. The spherical objective lens creates light having orthogonally related S and P-polarization states. In this embodiment, the aperture in the filter is aligned with one of the axes so that either the S or P-polarization components can be isolated.

Further objects and advantages of the subject invention will become apparent from reading the following detailed description taken in conjunction with the following drawings in which:

DETAILED DESCRIPTION OF THE PREFERRED EMBODIMENTS

Figure 2:
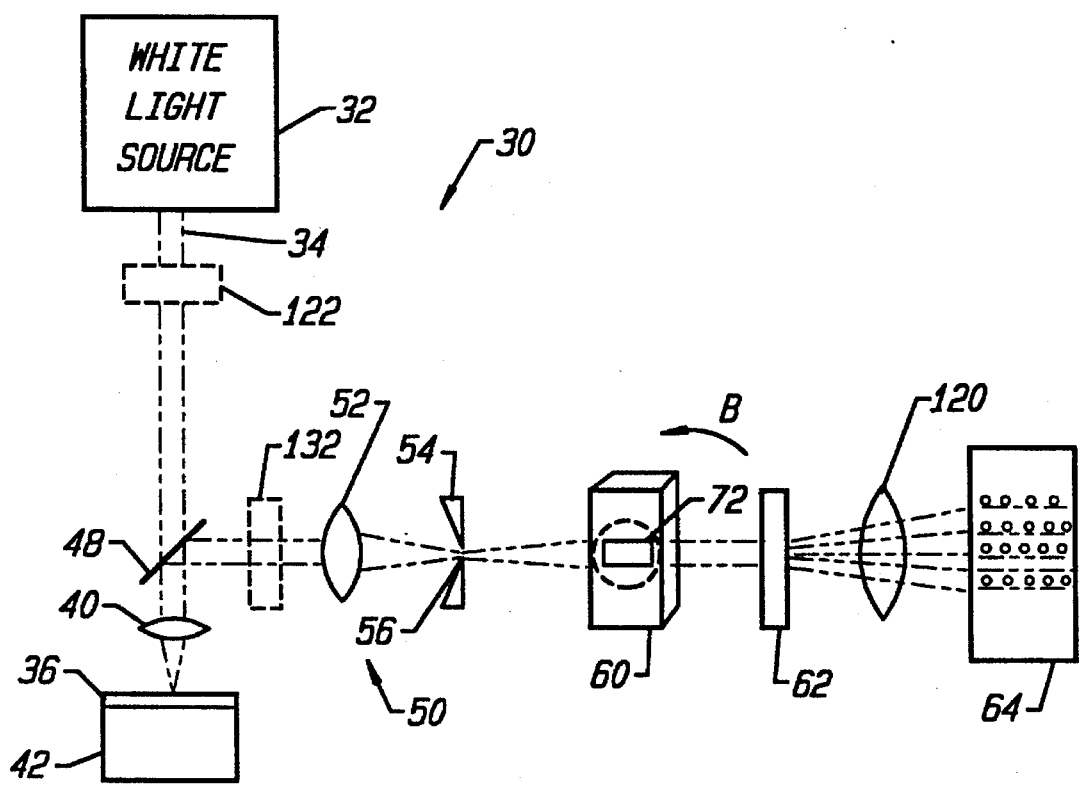
FIG. 2 is a schematic diagram of an optical measurement device incorporating the concepts of the subject invention.

Referring to FIG. 2 there is illustrated a system 30 for performing optical measurements in accordance with the subject invention. FIG. 2 includes a light source 32 for generating polychromatic or white light with multiple wavelength components. The non-coherent output 34 is focused onto the surface of the sample 36 via a spherical microscope objective lens 40. The sample can be mounted on a movable stage 42 to allow the probe beam to be scanned over the sample.

In the preferred embodiment, the probe beam 34 is directed normal to the sample surface and lens 40 has a high numerical aperture, on the order of 0.90. This high numerical aperture creates a large spread of angles of incidence on the surface of the sample 36. The angles of incidence can be traced within the reflected beam and simultaneously measured at the detector. As set forth in the assignees prior patents, the center ray corresponds to the central angle of incidence. The variation in the angle of incidence from the central angles varies in proportion to the increase in the radial position of the ray within the beam. As noted above with respect to equation (1), the location of any ray in the reflected probe beam corresponds to the sine of the angle of incidence.

After the probe beam is reflected from the sample surface, it is redirected towards the detection system by a beam splitter 48. Prior to reaching the detection system, the beam passes through a variable image filter 50. The filter 50 consists of a relay lens 52 and a plate 54. Plate 54 is located in the focal plane of relay lens 52 and includes an aligned aperture 56. The relay lens projects a magnified image of the surface of the sample into the plane of plate 54. The extent of magnification is given by the ratio of the focal length of lens 52 divided by the focal length of lens 40. A typical magnification would be about 60.

The aperture 56 is dimensioned so that it only transmits a portion of the relayed sample image. The amount of the image that is transmitted is defined by the size of the aperture divided by the magnification of the image. Thus, by adjusting the magnification provided by lens 52 as well as the size of the aperture 56, the size of the field of the sample which is imaged on the detector can be accurately controlled.

As noted above, using a high numerical aperture lens, the non-coherent light source can be focused down to a spot size of about 150 microns in diameter. In principal, using filter 50, image spots on the order of a micron can be achieved. To achieve this result, the diameter of the aperture would be 60 microns for a magnification of 60. It should be understood, however, that as the image of the spot is reduced, the energy reaching the detector is also reduced making measurement more difficult. Therefore, if larger image sizes are acceptable, (which is the case when high speed, average measurements are desired) more accurate results can be obtained with a larger image size. In practice, and as will be discussed with respect to FIG. 6, it is desirable for the filter 50 to include multiple apertures so that the image field can be easily selected by the operator to balance processing speed and detection accuracy with the desired spatial resolution.

In accordance with the subject invention, the reflected beam is then passed to the detection system. The detection system includes a filter 60, a dispersion element 62 and a detector 64. Suitable devices which could be used for detector 64 can be a two-dimensional photodiode array or a CCD camera.

As noted above, the prior art has suggested an approach which included the dispersion element and a two dimensional detector array. In the prior approach, the dispersion element functioned to angularly spread the beam as a function of wavelength. Optical devices which are suitable for the dispersion element include prisms, gratings and holographic plates. By spreading the beam, it is possible to separately measure the intensity of the light rays as a function of wavelength.

Figure 1:
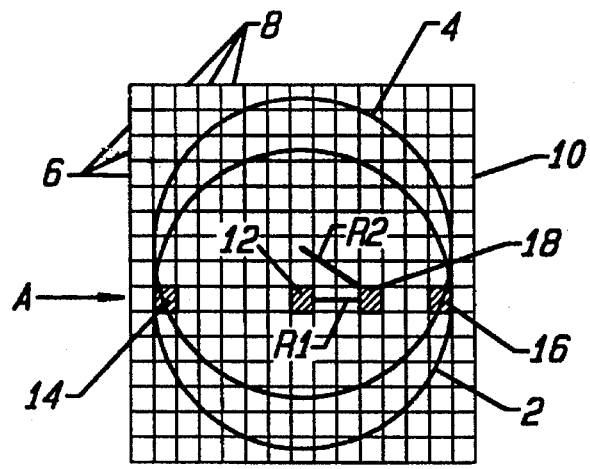
FIG. 1 is an illustration of a prior art approach for producing simultaneous multiple angle and multiple wavelength measurements.

The problems with the prior art approach were discussed above with reference to FIG. 1. These problems are overcome in the subject invention through the use of filter 60. Filter 60 includes an aperture 72 configured to transmit only a portion of reflected beam 54. In the preferred embodiment, aperture 72 is in the form of an elongated slit which is positioned along a diameter of the beam and is located in the relay image plane of the exit pupil of the objective lens 40. In this embodiment, lens 52 also serves to create this relay image. Aperture 72 is oriented in a manner to be perpendicular to the direction in which the dispersion element 62 angularly spreads the light. Preferably, the dimensions of the slit 72 are selected so that the image transmitted to the detector will be on the order of the dimensions of a row of detector elements. As will be discussed below, where the light source has been linearly polarized, the slit should be oriented in either the S or P-planes of polarization.

Figure 3:
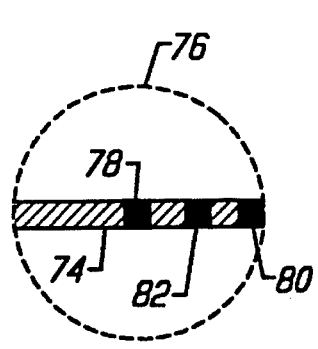
FIG. 3 is an illustration depicting the appearance of the probe beam after it passes through the filter 60 of FIG. 2.
Figure 4:
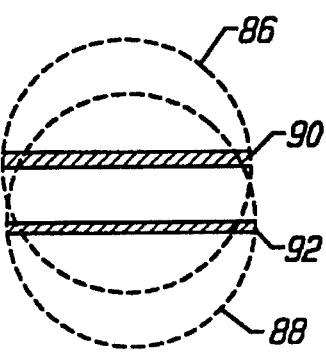
FIG. 4 is an illustration depicting the appearance of the probe beams associated with two different wavelengths after the probe beam has passed through the dispersion element 62 of FIG. 2.
Figure 5:
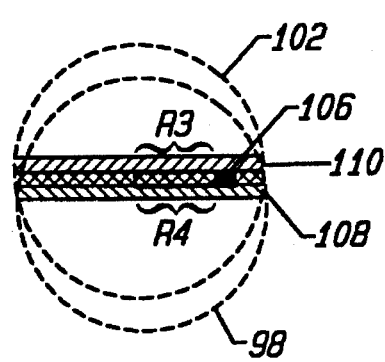
FIG. 5 is an illustration similar to FIG. 4 except that the wavelengths shown are closer together such that the separation between the probe beams is less.

The effect of filter 60 is illustrated in FIGS. 3 to 5. FIG. 3 illustrates the appearance of the beam just after it has passed through the aperture 72. As can be seen, only an elongated rectangular segment 74 is transmitted. The circular outline of the beam which has been blocked by filter 60 is shown in dotted line 76. Because the filter 60 is located in the relay image plane of the exit pupil of lens 40, the transmitted strip will include rays corresponding to all of the angles of incidence created by lens 40. In the preferred embodiment, point 78 will correspond to zero degrees, point 80 will correspond to 64 degrees and point 82 will correspond to 27 degrees.

FIG. 4 illustrates the beam 34 after it has passed through the dispersion element 62. Beams 86 and 88 represent two different wavelengths. The difference in the wavelengths is intended to be the same as the two beams illustrated in FIG. 1. Each wavelength illustrated in FIG. 4 includes a central rectangular transmitted segment 90, 92 carrying all of the angle of incidence information. As can be seen, for these two exemplary wavelengths, even though the circular beam foot prints would overlap, the transmitted segments do not, so there is no blurring of wavelength information for wavelengths having any significant difference. Thus, the row of detector elements aligned with segment 90 will provide full angle of incidence of information with no blurring of data from a second, disparate wavelength.

FIG. 5 illustrates the situation with beams 98 and 102 representing two, relatively closely spaced wavelengths. Where the two wavelengths are close, the dispersion element will provide only limited separation. However, the filter 60 of the subject invention substantially eliminates any measurement problems caused by the minimal overlap. More specifically, the aperture 72 in filter 60 is designed to transmit rays only along a single radial direction. Thus, the distance from the center of the beam to any given detector element will be substantially the same for each wavelength. Since this radial distance is the same, the angle of incidence of the rays falling on a given detector element will be the same for any wavelength.

This result can be seen in FIG. 5 taking detector element 106 as an example. The aperture 72 in filter 60 limits the transmission to two elongated segments 108 and 110 for beams 98 and 102 respectively. The radial distances between the center of each beam and the detector element 106 are shown as R3 and R4. As can be seen, these two radial distances are essentially the same, so that the angle of incidence of the rays striking the detector element 106 are the same.

As can be seen from FIGS. 4 and 5, the only blurring of data which occurs is limited to wavelengths that are very close together. Since the detection information along one row of pixels is limited to a very narrow band of wavelengths, sample analysis calculations based on wavelength will not be significantly impacted, particularly since the information at each detector element is limited to a single angle of incidence.

As can be appreciated from FIGS. 4 and 5, the elements across any individual row will provide simultaneous angle of incidence measurements for a given central wavelength. Each different row in the detector array will receive full angle of incidence information from a different central wavelength. Thus, by providing a two dimensional array of detectors, simultaneous measurements of multiple angles of incidence and at multiple wavelengths can be performed.

In practice, the dispersion element 62 may cause the pattern of the beam to spread in a rectangular fashion. In this case, it may be necessary to include suitable additional optical elements, such as a cylindrical lens 120 to recollimate the beam into a square format.

As described in U.S. Pat. No. 4,999,014, to improve the analysis capabilities of the device, it is desirable to measure light that is either S or P-polarized. One approach for achieving that goal is to linearly polarize the probe beam 34 using a conventional polarizing element. As described in the latter patent, when the linearly polarized light is focused on the sample surface, there will be one axis along which the light is purely S-polarized and an orthogonal axis along which the light is purely P-polarized. In the prior device, the multiple angle of incidence data for both the pure S and P-polarization information was simultaneously detected using two rows of detector elements oriented perpendicular to each other and aligned with the polarization axes.

In the preferred embodiment of the subject invention, it is also desirable to measure light which is either purely S or P-polarized. As in the prior patent, light from the source 32 would be linearly polarized using a standard polarizer (shown in phantom at 122). The filter 60 would then be oriented so that aperture 72 was aligned with one of the two pure polarization axes. The relative orientations of the dispersion element 62 and the array 64 would be suitably adjusted in the manner described above. In this manner, any row of detector elements will cover the full angle of incidence measurements at a central wavelength for the either pure S or P-polarization state.

Figure 7:
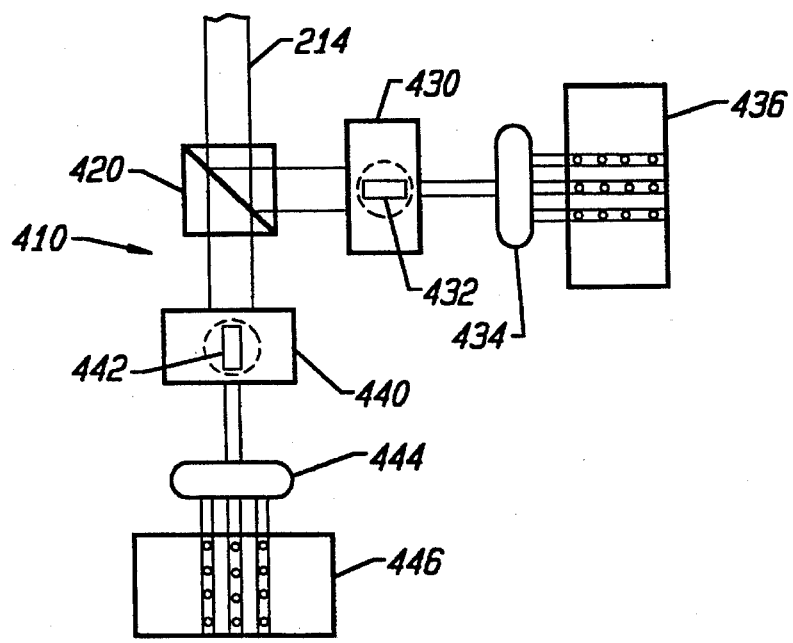
FIG. 7 is a schematic diagram of an alternate detection assembly suitable for simultaneous measurement at multiple angus of incidence and multiple wavelengths which can isolate pure polarization states of the probe beam.

One approach for deriving both S and P-information would be to take a second measurement after filter 60 and the dispersion element 62 have been rotated by ninety degrees as indicated by arrow B in FIG. 2. In this orientation, the remaining pure polarization state information could be detected. If it was desired to measure both polarization states simultaneously, a beam splitter could be inserted in the path of the reflected beam prior to the filter 60 to redirect a portion of the beam along another path. The other path would then be provided with a separate filter, dispersion element and array detector. The separate filter and dispersion element would be oriented orthogonally with respect to the filter and dispersion elements along the main path. This arrangement is illustrated in FIG. 7, discussed below.

The filter 60 of the subject invention has a further advantage when attempting to measure light of pure S or P-polarization. As noted above with respect to FIG. 1, in the prior art, an individual detector element will receive light from rays having different angles of incidence. Moreover, since the light from beam 4 is along a radial direction different from the radial direction of beam 2, it will also include a different combination of S and P-polarization states. If the row of elements designated by arrow A in FIG. 1 were oriented such that it was receiving pure polarization state light from beam 2, the prior art measurement would be further degraded because the light from beam 4 would contain a blend of S and P-polarization information.

The filter of the subject invention overcomes this problem as well. As noted above, the aperture 72 of filter 60 should be aligned with one of the two polarization states. In that case, the only light which will be transmitted will be either S or P-polarized. Any light of unwanted or a mixed polarization state will be blocked. Thus, the computational advantages associated with using pure polarized light can be maintained while simultaneously measuring information at different wavelengths.

The subject inventions can be utilized with either interferometric or ellipsometric devices. The main elements in FIG. 2 represent an interferometric device wherein the intensity variations of the reflected light rays are monitored. Details of the type of analysis which can be performed with this data are set forth in U.S. Pat. No. 4,999,014.

For operation as an ellipsometer, additional elements must be provided for determining the change in polarization state of the beam which occurs upon reflection off of the sample. In a basic arrangement, these additional elements would include the polarizer 122 and an analyzing section 132 (shown in phantom line). The polarizing and analyzing sections will include polarizing elements which can be rotated about the propagation axis of the beam. By knowing the relative azimuthal positions of these rotatable elements in conjunction with the intensity of measurements of detector 64, the change in polarization state of the rays in the beam can be determined. A discussion of simultaneous multiple angle of incidence ellipsometric analyses is set forth in U.S. Pat. No. 5,042,951.

It should be noted that while FIG. 2 illustrates both the improved variable image filter 50 and the detection system for simultaneous multiple angle of incidence and wavelength measurements, these two developments could be used separately. This independence can be appreciated with reference to FIG. 6 which illustrates one preferred form of an optical measurement system using a white light source and a multiple aperture variable image filter.

Figure 6:
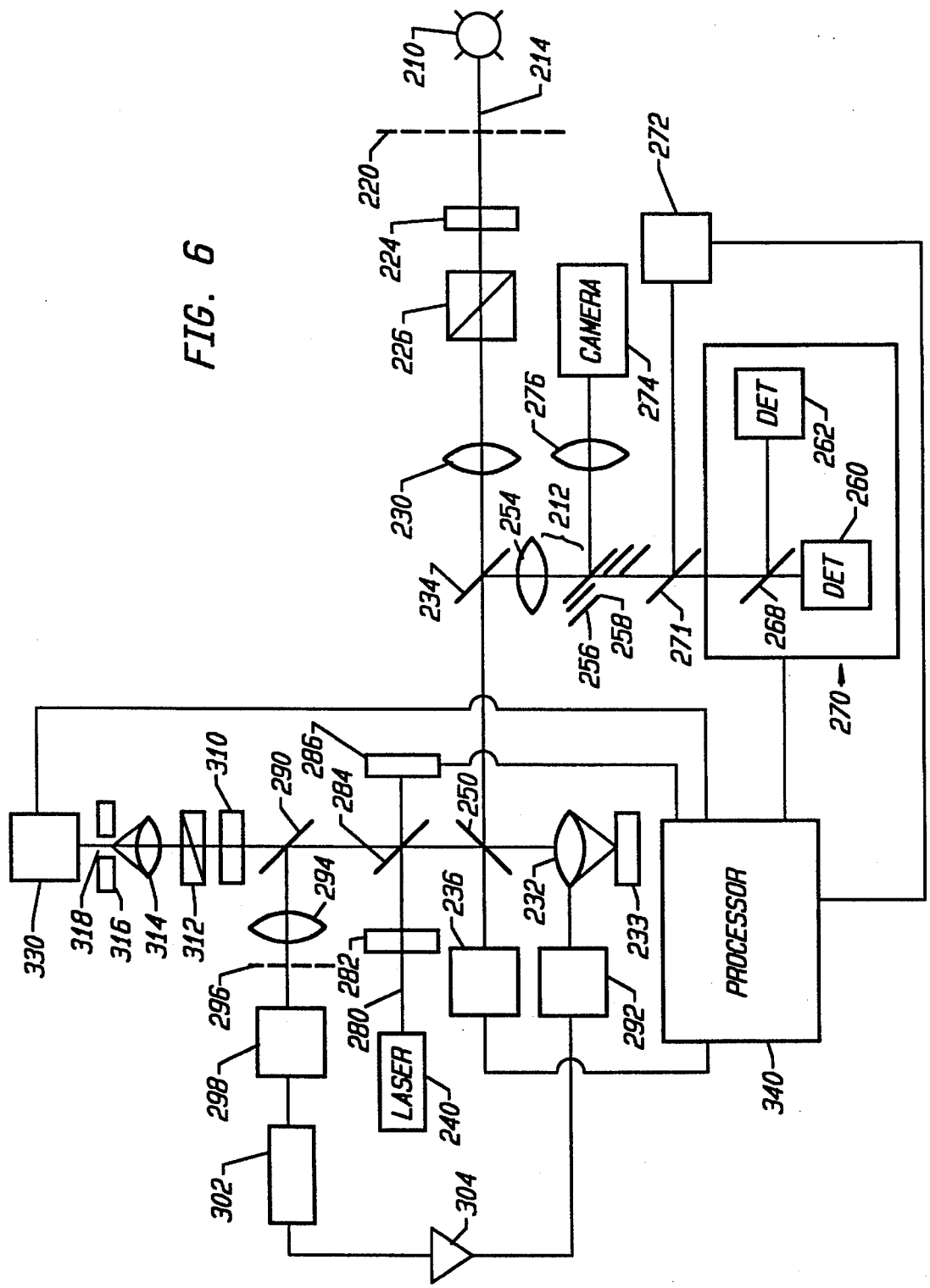
FIG. 6 is a schematic diagram of a more complete system incorporating the concepts of the subject invention wherein simultaneous multiple angle of incidence measurements can be made at a plurality of selected wavelengths.

FIG. 6 illustrates some of the additional elements which would be desirable in an simultaneous multiple angle of incidence interferometric measurement device 200. The device in FIG. 6 uses a non-coherent light source 210 and a variable image filter 212. However, the embodiment of FIG. 6 does not include a detection system suitable for simultaneous measurement at multiple wavelengths. The latter feature is disclosed as an alternative in FIG. 7.

In the device illustrated in FIG. 6, source 210 should be a bright, polychromatic or white light source such as a tungsten-halogen lamp. The light 214 from source 210 is then passed through one of a plurality of narrow band filters 220 for selecting one of a plurality of different wavelengths. The light is then passed through an on/off shutter 224 to polarizing beam splitter 226 for creating linearly polarized light.

The polarized light is then passed through lens 230 which relays an image of the source onto the pupil of spherical microscope objective lens 232. As in all embodiments, lens 232 is arranged to tightly focus the beam normal to the surface of the sample 233 to create a large spread of angles of incidence. The lens also functions to create light with substantial components of S and P-polarized light. One axis will contain predominantly S-polarized light while the orthogonal axis will contain predominantly P-polarized light. At intermediate angles between the S and P axes, the polarization states will be mixed.

Prior to reaching the objective, a portion of the light is transmitted through splitter 250 so that it will reach incident light detector 236. Detector 236 monitors the fluctuations in the output power of source 210 so that the measurements can be normalized.

The beam reflected from the sample is redirected back along the incoming path by splitter 250 until it strikes splitter 234 where it is redirected downwardly to the variable image filter 212. As discussed above, filter 212 includes a relay lens 254 which projects an image of the surface sample into the plane of plate 256. In this embodiment, the filter includes a plurality of interchangeable plates each having a different size apertures 258. By this arrangement, the operator can select the size of the image field to be projected onto the principle detectors 260 and 262. In the preferred embodiment, the plates 256 may be mounted on a rotatable wheel (not shown). The desired aperture can be positioned in the beam path by adjusting the rotational angle of the wheel.

After passing through filter 212, the beam is directed to a beam splitter 268 for dividing the beam along two paths and to detectors 260 and 262. Each detector 260, 262 consists of a one dimensional linear array of photodetector elements. One array is oriented to provide full angle of incidence information for S-polarized light. The other array is oriented perpendicular to the first array and will provide full angle of incidence information for P-polarized light. By this arrangement, simultaneous multiple angles of incidence information can be generated at a plurality of wavelengths in a sequential manner. This information will allow for an interferometric evaluation of thin film samples. In this approach, the processor will evaluate the sample based on the simultaneous angular dependent intensity measurements made by the detectors. These intensity measurements are a function of the interference effects created by the interaction of the probe beam with the surface of the thin film and the interface between the thin film and the sample. These simultaneous angle of incidence measurements will be repeated for each of a plurality of different wavelengths selected by filters 220.

In the embodiment illustrated in FIG. 6, two detectors, each having a linear area of detector elements are utilized. As an alternative, a single detector head could be used having two orthogonally disposed linear arrays. The latter type of detector head is described in U.S. Pat. No. 4,999,014. As a further alternative, a full two dimensional array of the type shown in FIG. 2 could be used.

As will be discussed below with respect to FIGS. 7 through 9, other forms of the detector elements (enclosed in box 270) can also be used. For example, a detector arrangement designed to measure different wavelengths simultaneously may be employed in which the use of the narrow band filters 220 can be eliminated.

In a preferred embodiment, a portion of the light passing through filter 212 is picked off by a splitter 271 and directed to full power detector 272. As discussed in detail in the above identified patents of the assignee, measurement ambiguities from the multiple angle of incidence measurements can be resolved using an additional full beam power measurement.

Operation of the device can be facilitated through the use of a vision system. In this illustrated embodiment, plates 256 are made reflective and redirect, to a camera 274, that portion of the image which is larger than the associated aperture 258 in plate 256. The image received by the camera 274 will have a central dark spot corresponding to that portion of the light transmitted by the aperture 258. A lens 276 is provided to image the sample surface onto the camera.

In the preferred embodiment, it is envisioned that the white light measurement system will be combined with the elements for a laser detection system as described in U.S. Pat. Nos. 4,999,014 and 5,181,080, assigned to the same assignee as herein and incorporated by reference. In this system, a laser diode 240 is used to generate a linearly polarized probe beam 280. The wavelength of the output is preferably on the order of 650 to 820 nm. The probe beam 280 is passed through an on/off shutter 282 to a beam splitter 284. A portion of the beam passes through splitter 284 and falls on incident power detector 286 for monitoring fluctuations in the output of the laser diode.

The remainder of the beam is redirected down through beam splitter 250 to lens 232 and focused on the sample 233. Since the beam from the laser is monochromatic and reasonably coherent, it can be focused down to a spot size on the order of one micron by lens 232. A portion of the reflected beam is redirected by splitter 290 to an autofocus system used to maintain the focus of the lens 232 and onto sample 233. In the assignees present commercial devices wherein this type of autofocus system is used, the lens focus spacing can be maintained to less than one hundredth of a micron.

The autofocus system includes servo mechanisms 292 for varying the vertical position of the lens 232. The servo is driven by an analog detection loop which determines if the lens 232 is properly focusing the probe beam. The detection loop includes the reflected light which is focused by a lens 294 through a chopper wheel 296 located in the focal plane of lens 294. The light passing the chopper wheel 296 falls on a split-cell photodetector 298. If the lens 232 is out of focus, there will be a phase difference in the light striking the two sides of the split cell 298 which is detected by a phase detector 302. The phase difference is used as an input to an amplifier 304 which in turn drives the servo 292. This approach to autofocusing is known as the automated Foucault knife edge focus method.

In the illustrated embodiment, both specific multiple angle of incidence information as well as a signal which represents an integration of the intensity of all rays having different angles of incidence is measured for the laser probe beam 280. To obtain the specific angle of incidence information, a portion of the returning reflected probe laser beam is redirected by splitter 250 to splitter 234. Splitter 234 redirects the probe laser beam downwardly towards detector arrays 260 and 262. By utilizing the same detector arrays that were provided for detecting the polychromatic light, simultaneous multiple angle of incidence information can be generated for both S and P-polarizations of the laser light. As discussed above, the total reflected power of the beam can be measured by detector 272.

Where the detector arrays 260, 262 are used to measure light from both the white light source 210 and the laser 240, the measurements should be taken sequentially, with only one source emitting radiation at a time. Sequential operation is achieved using shutters 224 and 282. Since the power output of the two sources will be different, it will be necessary to adjust the gain of the detectors for the different measurements.

When detecting light from the probe laser beam, the filter 212 would be arranged to image a twenty-five micron size spot. By this arrangement, the filter 212 will function in a manner analogous to the filter described in the prior U.S. Pat. No. 5,159,412, where light reaching the detector from areas beyond the focused spot on the sample is minimized.

In order to obtain ellipsometric information from an integration of all rays having different angles of incidence with respect to the sample surface, the reflected probe beam light from laser 240 is also passed upwardly, past beam splitter 290 to a quarter-wave plate 310 for retarding the phase of one of the polarization states of the beam by ninety degrees. The beam is then passed through a linear polarizer 312 which functions to cause the two polarization states of the beam to interfere with each other. In order to maximize the desired signal, the axis of the polarizer should be oriented at an angle of 45 degrees with respect to the fast and slow axes of the quarter-wave plate.

The light is then passed through an image filter including a relay lens 314 and plate 316 having an aperture 318. The filter is used to prevent spurious reflections from beyond the focused spot from reaching detector 330. Detector 330 is a photocell having four radially disposed quadrants. Each quadrant will generate an output signal proportional to the magnitude of the power of the probe beam striking the quadrant. This signal represents an integration of the polarization interference signals from of all the rays having different angles of incidence with respect to the sample surface. The quadrant arrangement is configured to generate independent signals along two orthogonal axes. As described in detail in U.S. Pat. No. 5,181,080, by subtracting the sum of the outputs of the diametrically opposed quadrants, a signal can be obtained which is linearly proportional to the thickness of the thin film. For very thin films in particular, this approach provides an accurate measurement of the ellipsometric parameter δ which is related to both the optical thickness of the thin film as well as the extinction coefficient of the substrate.

In the preferred embodiment, a processor 340 is provided for evaluating the output from detectors 236, 260, 262, 272, 286 and 330 to provide unambiguous information about the characteristics of the sample.

The apparatus 200 of FIG. 6 can be modified to simultaneously measure multiple wavelength information. The detector arrangement 410 for implementing this approach is illustrated in FIG. 7. The detector arrangement in 410 would replace (or be used in conjunction with) the elements indicated at 270 in FIG. 6. When using the detector arrangement of FIG. 7, the wavelength selective filters 220 of the FIG. 6 embodiment would not be used.

The detector arrangement 410 is configured to simultaneously evaluate both S and P-polarization states. Accordingly, the polychromatic light 214 is passed to a beam splitter 420 which divides the light into two beams. One part of the beam passes through a filter 430 having an aperture 432 aligned with the axis of one of the two pure polarization states. Filter 430 is located in the image plane of the exit pupil of lens 232. In this embodiment, lens 254 creates this relay image. Dispersion element 434 is oriented to angularly spread the light in a direction perpendicular to the orientation of aperture 432. Detector 436 includes a two dimensional array of detector elements and is configured to simultaneously measure angle of incidence and wavelength information of the selected polarization state. The filter 430, dispersion element 434 and detector 436 are identical to that described in FIG. 2.

In order to simultaneously obtain data for the remaining polarization state, a second set of detector elements are provided in the alternate path of the beam. As seen in FIG. 7, a filter 440 (with aperture 442), dispersion element 444 and detector 446 are provided. The difference in this arm of the optical lay-out is that the filter 440 and dispersion element 444 are rotated ninety degrees with respect to the filter 430 and dispersion element 434. By this arrangement, the filter 440 will isolate the light having the remaining polarization state for measurement by the detector.

As noted above, it is also possible to apply the concepts of the simultaneous multiple wavelength detection system to ellipsometric optical devices as described in U.S. Pat. Nos. 5,042,951 and 5,181,080. FIG. 8 illustrates the application of the teachings of U.S. Pat. No. 5,042,951, wherein specific simultaneous angle of incidence measurements are made at multiple wavelengths to derive the ellipsometric parameters. In this Figure, the components 510 could replace (or be used in conjunction with) the optical-components 270 of FIG. 6.

Figure 8:
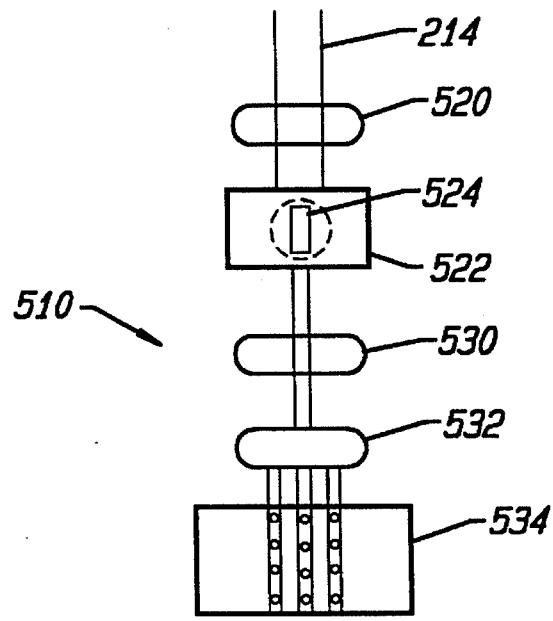
FIG. 8 is a schematic diagram of another alternate detection assembly suitable for deriving ellipsometric parameters based on the simultaneous measurement of both multiple angle of incidence and multiple wavelength information.

As seen in FIG. 8, the polychromatic beam 214 is first passed through a quarter wave retarder 520. The quarter wave retarder changes the linear polarization of the beam into circular polarization. A retarder which is suitable for use over a wide wavelength range would include a Fresnel rhomb of the type available from Spindler and Hoyer.

The beam would than be passed through a filter 522 having an elongated aperture 524. As in the previous embodiments, filter 522 is located in the relay image plane of the objective 232. The beam is then passed through a rotating polarizer 530 and dispersion element 532 and onto a two-dimensional photodetector array 534.

The derivation of the ellipsometric parameters ψ and δ are obtained as a function of both the incidence angle θ and wavelength. The filter 522, dispersion element 532 and the two-dimensional array 534 permit the simultaneous measurement at multiple wavelengths. The derivation of ψ and δ at each of the different wavelengths with respect to the angles of incidence θ is similar to that described in U.S. Pat. No. 5,042,951 and will be briefly discussed herein.

To derive ψ and δ, a plurality of measurements are made at various rotational positions of the polarizer 530. The polarizer is rotatable about an azimuthal angle φ with respect to the surface of the sample. In order to derive the first ellipsometric parameter ψ, measurements can be taken at φ=0 degrees and φ=σ/2. The measured signal at φ=0 is defined as follows:

$$S_x(0) = |R_s|^2 \tan^2 \psi = |R_p|^2 \qquad (2)$$

The measured signal at φ=π/2 is given by:

$$S_x(\pi/2) = |R_s|^2 \qquad (3)$$

and therefore the value for ψ is $$\tan^2 \psi = \frac{S_x(0)}{S_x(\pi/2)} \qquad (4)$$

In order to derive δ, two additional measurements can be taken at φ=π/4 and at φ=−π/4. At φ=π/4, the measured signal is given by:

$$S_x(\pi/4) = \tfrac{1}{2}|R_s|^2 [\tan^2 \psi + 1 + 2 \tan \psi \sin \delta] \qquad (5)$$

and at φ=−π/4 the measured signal is given by:

$$S_x(-\pi/4) = \tfrac{1}{2}|R_s|^2 [\tan^2 \psi + 1 - 2 \tan \psi \sin \delta] \qquad (6)$$

Taking the difference between equations 5 and 6 we obtain:

$$S_x(\pi/4) - S_x(-\pi/4) = 2 |R_s|^2 \tan \psi \sin \delta \qquad (7)$$

and taking the sum of δ equations 5 and 6 we obtain:

$$S_x(\pi/4) + S_x(-\pi/4) = |R_s|^2 [\tan^2 \psi + 1] \qquad (8)$$

and consequently δ can be expressed as:

$$\sin \delta = \frac{S_x(\pi/4) - S_x(-\pi/4)}{S_x(\pi/4) + S_x(-\pi/4)} \left[ \frac{(\tan^2 \psi + 1)}{2 \tan \psi} \right] \qquad (9)$$

Since the value for ψ has been obtained with the first two measurements using equation 4, δ can be calculated using equation 9 and the second two measurements. By using synchronous detection, highly accurate measurements of the ellipsometric parameters ψ and δ can be made as a function of angle of incidence and of wavelength.

The ellipsometric technique described in U.S. Pat. No. 5,181,080, which generates a signal that represents an integration of intensities at multiple angles of incidence, can be enhanced with the teachings of the subject invention to allow simultaneous measurements at multiple wavelengths. FIG. 9 illustrates the components 610 for achieving this result. Components 610 could replace (or be used in conjunction with) the optical components 270 of FIG. 6.

Figure 9:
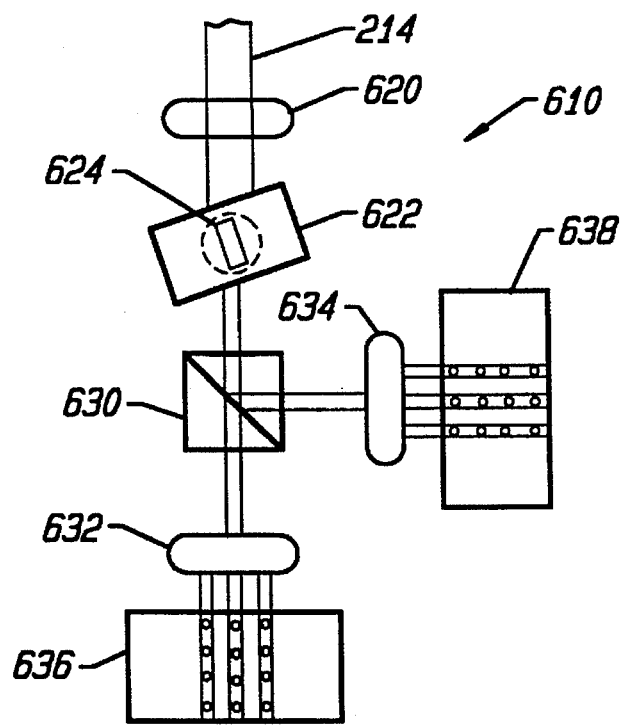
FIG. 9 is a schematic diagram of another alternate detection assembly suitable for simultaneous measurement of integrated ellipsometric data at multiple wavelengths as well as specific angle of incidence information.

As seen in FIG. 9, the polychromatic beam 214 is passed through a quarter-wave retarder 620 such as a Fresnel rhomb positioned so that it will retard one of the polarization states of the beam by ninety degrees. The beam is than passed through filter 622 having an elongated aperture 624. A portion of the beam is then passed through a polarizing splitter 630 which creates interference between the two polarization states. Splitter 630 also creates two beams directed along two different paths. One beam will be composed of right-hand circularly polarized components of light reflected from the sample. The other beam will be composed of left-hand circularly polarized components of the reflected beam. Both the first and second beam paths include a dispersion element 632, 634 and a two-dimensional detector array 636, 638.

As described in U.S. Pat. No. 5,181,080, the data with the most information content will fall along an axis intermediate the axes of the initial pure polarization states. It is along this axis that the interference between the two polarization states is maximized. Therefore, in the embodiment of FIG. 9, the filter 622 is positioned such that the elongated aperture 624 is oriented at angle of 45 degrees with respect to the initial polarization of the incident beam. In this manner, only the portion of the light having the most relevant information will be transmitted. As in the other embodiments, the dispersion elements 632 and 634 are oriented so that the angular spreading of the wavelength information is perpendicular to the orientation of the aperture 624.

The polarizing beam splitter 630 separates the beam 214 into two equal components, one right-hand circularly polarized, the other left-hand circularly polarized. Each row of detector elements will contain information about the range of angles of incidence at a given narrow band of wavelengths. In order to provide a signal which represents an integration of this information, the signals coming from a given row in detector 636 can be subtracted from a corresponding row in detector 638. This is similar to the subtraction of quadrant information in the quad cell detector used in U.S. Pat. No. 5,181,080. As noted therein, the power hitting corresponding detector elements in each of the two detectors arrays is identical except for a sign change in a term that varies with the ellipsometric parameter $\delta$. Thus, by subtracting the signal from one row of elements from the corresponding row in the other detector, a value can be obtained that is linear with respect to $\delta$ which itself is proportional to the thickness of a thin film.

The detector arrangement of FIG. 9 is not limited to the generation of an integration signal but can also be used to provide information with respect to specific angles of incidence. To obtain this data, the output from a single pixel in one array 636 can be subtracted from the output generated by the corresponding pixel in the other array. The location of the pixel with respect to the radial position in the beam can be used to map the angle of incidence of the associated ray. This approach will provide specific angle of incidence information without using a rotating polarizer as shown in FIG. 8.

While the subject invention has been described with reference to a number of preferred embodiments, various changes and modifications could be made therein, by one skilled in the art, without varying from the scope and spirit of the subject invention as defined by the appended claims.

We claim:

1. An apparatus for evaluating a characteristic of a sample comprising:

a polychromatic light source means for generating at least one probe beam directed to reflect off and interact with the sample surface;

a first detector for measuring changes in a magnitude of the reflected probe beam resulting from the interaction with the sample and generating first output signals corresponding to a plurality of different wavelengths;

second detector for analyzing a change in polarization state of the reflected probe beam resulting from the interaction with the sample and generating second output signals corresponding to a plurality of different wavelengths, with said second output signals being separate and independent from the first output signals; and processor for deriving information about a characteristic of the sample based on a combination of the first output signals representing the change in magnitude measurement as a function of wavelength and the second, independent output signals representing the polarization state analysis as a function of wavelength such that ambiguities in the result are minimized.

2. An apparatus as recited in claim 1 wherein there is only a single probe beam measured by both said first and second detectors.

3. An apparatus as recited in claim 1 wherein said light source means includes two separate polychromatic light sources for generating two separate probe beams with the first detector measuring one of the probe beams and the second detector measuring the other probe beam.

4. An apparatus as recited in claim 1 wherein said probe beam is directed to the sample such that various rays create a spread of angles of incidence and said first detector generates output signals corresponding to a plurality of angles of incidence.

5. An apparatus as recited in claim 4 wherein said first detector generates output signals corresponding to a plurality of angles of incidence.

6. An apparatus as recited in claim 1 wherein said probe beam is directed to the sample such that various rays create a spread of angles of incidence and said second detector generates output signals corresponding to a plurality of angles of incidence.

7. An apparatus as recited in claim 1 wherein the output signals generated by said second detector represent an integration of rays having multiple angles of incidence.

8. An apparatus as recited in claim 1 wherein said first output signals corresponding to a plurality of different wavelengths are measured simultaneously.

9. An apparatus as recited in claim 1 wherein said second output signals corresponding to a plurality of different wavelengths are measured simultaneously.

* * * * *